US011519042B2

(12) United States Patent
Perot et al.

(10) Patent No.: US 11,519,042 B2
(45) Date of Patent: Dec. 6, 2022

(54) METHOD FOR THE DIAGNOSIS OR PROGNOSIS, IN VITRO, OF LUNG CANCER

(71) Applicant: BIOMERIEUX, Marcy l'Etoile (FR)

(72) Inventors: Philippe Perot, Lyons (FR); François Mallet, Villeurbanne (FR); Cécile Montgiraud, Unieux (FR); Nathalie Mugnier, Lyons (FR)

(73) Assignee: BIOMERIEUX, Marcy l'Etoile (FR)

( * ) Notice: Subject to any disclaimer, the term of this patent is extended or adjusted under 35 U.S.C. 154(b) by 197 days.

(21) Appl. No.: 14/367,872

(22) PCT Filed: Dec. 20, 2012

(86) PCT No.: PCT/FR2012/053012
§ 371 (c)(1),
(2) Date: Jun. 20, 2014

(87) PCT Pub. No.: WO2013/093353
PCT Pub. Date: Jun. 27, 2013

(65) Prior Publication Data
US 2015/0119265 A1    Apr. 30, 2015

(30) Foreign Application Priority Data

Dec. 20, 2011 (FR) ..................... 11/62089

(51) Int. Cl.
*C12Q 1/70* (2006.01)
*C12Q 1/6886* (2018.01)
*G01N 33/574* (2006.01)

(52) U.S. Cl.
CPC .......... *C12Q 1/702* (2013.01); *C12Q 1/6886* (2013.01); *G01N 33/57423* (2013.01); *C12Q 2600/118* (2013.01); *C12Q 2600/158* (2013.01)

(58) Field of Classification Search
CPC ............... C12Q 1/702; C12Q 1/6886; C12Q 2600/118; C12Q 2600/158; G01N 33/57423
See application file for complete search history.

(56) References Cited

U.S. PATENT DOCUMENTS

| | | | | |
|---|---|---|---|---|
| 2001/0053519 | A1* | 12/2001 | Fodor .................. | B01J 19/0046 435/6.11 |
| 2009/0297530 | A1 | 12/2009 | Wang-Johanning | |
| 2014/0349857 | A1* | 11/2014 | Mallet ............... | G01N 33/57419 506/2 |
| 2014/0370503 | A1* | 12/2014 | Mallet ................. | C12Q 1/6886 435/6.11 |
| 2015/0065368 | A1* | 3/2015 | Perot .................... | C12Q 1/6886 506/9 |
| 2015/0065369 | A1* | 3/2015 | Perot .................... | C12Q 1/6886 506/9 |
| 2015/0119265 | A1* | 4/2015 | Perot ..................... | C12Q 1/702 506/9 |

FOREIGN PATENT DOCUMENTS

| | | | | |
|---|---|---|---|---|
| EP | 2 340 851 A1 | 7/2011 | | |
| WO | WO 0246477 A2 | * | 6/2002 | ........... C07K 14/005 |
| WO | WO 02099055 A2 | * | 12/2002 | ............... C12Q 1/42 |

OTHER PUBLICATIONS

Stauffer (Cancer Immunity (2004) vol. 4, p. 2).*
Benner et al (Trends in Genetics (2001) vol. 17, pp. 414-418).*
Greenbaum et al (Genome Biology 2003, vol. 4, article 117, pp. 1-8).*
Cheung et al (Nature Genetics, 2003, vol. 33, pp. 422-425).*
Saito-Hisaminato et al. (DNA research (2002) vol. 9, pp. 35-45).*
Wu (Journal of Pathology, 2001, vol. 195, pp. 53-65).*
Munroe et al (Molecular and Cellular Biology (1990) vol. 10, pp. 3441-3455).*
Perot et al (PLOS One (2012) vol. 7, pp. e40194.*
NCBI Blast ( http://blast.ncbi.nlm.nih.gov/Blast.cgi, May 30, 2016.*
Fong (Cancer Research (1997) vol. 57, pp. 2256-2267).*
Meyerson (Nature Reviews Oct. 2010 pp. 685-696).*
Genbank Accession AL137063.11 (https://www.ncbi.nlm.nih.gov/nuccore/9581554?sat=43&satkey=4423065, May 18, 2005).*
Lower ( Proceedings National Academy of Science (1996) vol. 93, pp. 5177-5184).*
Gimenez (Nucleic Acids Research (2010)vol. 38, pp. 2229-2246).*
Andersson (International Journal of Oncology (1998) vol. 12, pp. 309-313).*
Wada (Genes & Development (1998) vol. 12, pp. 343-356).*
Blast RIDJ22ZMRY201R (https://blast.ncbi.nlm.nih.gov/Blast.cgi, downloaded Jun. 13, 2018).*
Kovalskaya (virology (2006) vol. 346, pp. 373-378).*
Gen Bank accession AC011895.4 (https://www.ncbi.nlm.nih.gov/nucleotide/AC011895.4?report=genbank&log$=nuclalign&blast_rank=1&RID=V38VGX9A015, Apr. 29, 2003).*
Genbank accession AC068643.27 (https://www.ncbi.nlm.nih.gov/nuccore/AC068643.27, Jan. 29, 2003).*
Bustin (Journal of Molecular Endocrinology (2002) vol. 29, pp. 23-29.*
Merriam Webster.com (https://www.merriam-webster.com/dictionary/suspect, downlaoaded May 20, 2020).*
Ahn ( Mol Cells (2009) vol. 28, pp. 99-103).*
Yi (Genes Gene System (2007) vol. 82, pp. 89-8).*

(Continued)

*Primary Examiner* — Steven Pohnert
(74) *Attorney, Agent, or Firm* — Oliff PLC (57) ABSTRACT

The subject matter of the present invention is a method for the diagnosis or prognosis, in vitro, of lung cancer, which includes a step of detecting at least one expression product of at least one HERV nucleic acid sequence, a method for use of said nucleic acid sequences, which have been isolated, as a molecular marker or molecular markers, and a kit including at least one binding partner specific for at least one of the expression products of the HERV nucleic acid sequences.

16 Claims, 2 Drawing Sheets
Specification includes a Sequence Listing.

(56) References Cited

OTHER PUBLICATIONS

Ishida (Cancer Immunity (2008) vol. 8, pp. 1-10).*
Yi (Cancer letters (2004) vol. 211, pp. 89-96).*
Yi cancer Letters (2006) vol. 231, pp. 228-239).*
Yi (J Hum Genet (2007) vol. 52, pp. 285-296).*
Ahn, Kung et al., "Structural and Quantitative Expression Analyses of HERV Gene Family in Human Tissues," Molecules and Cells, Aug. 31, 2009, vol. 28, No. 2, pp. 99-103.
Subramanian, Ravi et al., "Identification, Characterization, and Comparative Genomic Distribution of the HERV-K (HML-2) Group of Human Endogenous Retroviruses," Retrovirology, 2011, vol. 8, No. 1, pp. 1-22.
Gimenez, Juliette et al., "Custom Human Endogenous Retroviruses Dedicated Microarray Identifies Self-Induced HERV-W Family Elements Reactivated in Testicular Cancer Upon Methylation Control," Nucleic Acids Research, 2010, vol. 38, No. 7, pp. 2229-2246.
Paces, Jan et al., "HERVd: the Human Endogenous RetroViruses Database: Update," Nucleic Acids Research, 2004, vol. 32, pp. 1.
"Human DNA Sequence From Clone RP1-104L14 on Chromosome 6 contains the 3' End of the AKAP7 Gene for a Kinese (PRKA) Anchor Protein 7, Complete Sequence," XP002702741, pp. 1-42.
Liang, Qiaoyi et al., "Identification of a Novel Human Endogenous Retrovirus and Promoter Activity of its 5' U3," Biochemical and Biophysical Research Communications, 2009, vol. 382, No. 2, pp. 468-472.
Nickerson, Deborah A. et al., "DNA Sequence Diversity in a 9.7-kb Region of the Human Lipoprotein Lipase Gene," Nature Genetics, vol. 19, Jul. 1998, vol. 19, pp. 233-240.
Navarro, Gonzalo et al., "Flexible Pattern Matching in Strings," Cambridge University Press, 2002.
Irizarry, Rafael A., "Exploration, Normalization, and Summaries of High Density Oligonucleotide Array Probe Level Data," Biostatistics, 2003, vol. 4, No. 2, pp. 249-264.
Johnson, W. Evan et al., "Adjusting Batch Effects in Microarray Expression Data Using Empirical Bayes Methods," Biostatistics, 2007, vol. 8, No. 1, pp. 118-127.
Tusher, Virginia Goss et al., "Significance Analysis of Microarrays Applied to the Ionizing Radiation Response," PNAS, Apr. 24, 2001, vol. 98, No. 9, pp. 5116-5121.
Storey, John D. et al., "Statistical Signficance for Genomewide Studies," PNAS, Aug. 5, 2003, vol. 100, No. 16, pp. 9440-9445.

* cited by examiner

METHOD FOR THE DIAGNOSIS OR PROGNOSIS, IN VITRO, OF LUNG CANCER

Endogenous retroviruses constitute the progeny of infectious retroviruses which have integrated, in their proviral form, into germ line cells and which have been transmitted via this means into the genome of the progeny of the host.

The sequencing of the human genome has made it possible to reveal the extremely high abundance of transposable elements or derivatives thereof. In fact, repeated sequences represent close to half the human genome and endogenous retroviruses and retrotranposens make up 8% of said genome, with the number of elements, at the current time, coming to more than 400,000.

The abundance of endogenous retroviral elements (ERVs) currently present in the human genome is the result of about 100 endogenizations which have successfully taken place during the course of the evolution of the human line. The various waves of endogenization are spread out over a period ranging from 2 to 90 million years before our era and have been followed by the expansion of the number of copies via phenomena of the "copy/paste" type with the possibility of the appearance of errors, resulting, starting from an ancestral provirus, in the formation of a family of HERVs, i.e. a set of elements which exhibit sequence homologies. The oldest elements, those of the HERV-L family, supposedly became integrated before the emergence of mammals. Two families, HERV-F and HERV-H, appeared during the period when the first primates were mating their appearance. The HERV-FRD and HERV-K(HML-5) families, integrated 40 to 55 million years ago, are specific for higher primates. On the other hand, the HERV-W and HERV-E families, for example, became integrated 5 to 10 million years later, after the separation with New World monkeys, and are specific for the Catarrhini (Hominoids and Cercopithecidae).

The ERV sequences are represented on all the chromosomes, with a varying density according to the families, and there is no correlation between the physical proximity of ERVs and their phylogenetic proximity.

For a long time, ERVs have been considered to be parasites or to be simple DNA waste. Nevertheless, the impact of ERVs on the organism is not only limited to their past participation in modeling the genome or to deleterious recombinations which stay still provide support.

The abundance and the structural complexity of ERVs makes analyses of their expression very complicated and often difficult to interpret. The detection of HERV expression say reflect the transcriptional activation of one or more loci within the same family. The activated locus or loci may in addition vary according to the tissue and/or the context.

The present inventors have now discovered and demonstrated that nucleic acid sequences corresponding to precisely identified loci of endogenous retroviral elements are associated with rang career and that these sequences are molecular mar here of the pathological condition. The sequences identified are either proviruses, i.e. sequences containing all or part, of the gag, pol and env genes flanked in the 5' and 3' positions by long terminal repeats (LTRs), or all or part of the LTRs or of the genes isolated. The DNA sequences identified are respectively referenced as SEQ ID NO: 1 to 242 in the sequence listing, their chromosomal location is identified in the table below (NCBI 36/hg18), as are their expression, overexpression or underexpression represented by the "expression ratio" between cancer sample and normal sample. When the expression of the nucleic acid or the change in the expression of the nucleic acid is specific for lung tissue, this information is indicated by the sorbet "x" in the target tissue column. This signifies that, it an expression or a change in expression of the nucleic acid concerned is determined in a biological compartment other than lung tissue, this represents, remotely, a signature of lung cancer. The DNA sequences identified as being specific for lung tissue are respectively referenced as (SEQ ID NOs: 4, 5, 7, 9, 10, 12, 20, 25 and 40 in the sequence listing. The DNA sequences identified as being not specific for lung tissue are respectively referenced as SEQ ID NOs: 1, 2, 3, 6, 8, 11, 13, 14, 15, 16, 17, 18, 19, 21, 22, 23, 24, 26, 27, 28, 29, 30, 31, 32, 33, 34, 35, 36, 37, 38, 39, 41, 42, 43, 44, 45, 46, 47, 48, 43, 50, 51, 52, 53, 54, 55, 26, 27, 28, 29, 60, 61, 62, 63, 64, 63, 66, 67, 63, 69, 70, 71, 72, 73, 74, 75, 76, 77, 78, 79, 90, 81, 82, 83, 84, 85, 86, 87, 88, 89, 90, 91, 92, 93, 94, 95, 96, 97, 98, 99, 100, 101, 102, 103, 104, 102, 106, 107, 108, 109, 110, 111, 112, 112, 114, 115, 116, 117, 118, 119, 120, 121, 122, 123, 124, 125, 126, 127, 128, 129, 130, 131, 132, 133, 134, 133, 136, 137, 138, 132, 140, 141, 142, 143, 144, 143, 146, 147, 148, 149, 150, 151, 152, 153, 154, 155, 156, 157, 158, 159, 160, 161, 162, 163, 164, 165, 166, 167, 168, 169, 170, 171, 172, 173, 174, 173, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 213, 216, 217, 218, 219, 220, 221, 222, 223, 224, 225, 226, 227, 228, 229, 230, 231, 282, 233, 234, 235, 236, 237, 238, 239, 240, 241 and 242.

TABLE

| SEQ ID NO: | Chromosomal location | Target tissue | Cancer/normal expression ratio |
|---|---|---|---|
| 1 | (+) chr 19: 57753757-57754726 | | −4.8 |
| 2 | (−) chr 3: 32480101-32483411 | | −3.9 |
| 3 | (+) chr 3: 135222763-135223084 | | −3.7 |
| 4 | (+) chr 6: 131686129-131689771 | x | −3.5 |
| 5 | (−) chr X: 91414738-91420449 | x | −3.2 |
| 6 | (+) chr 7: 100274888-100276065 | | 3.2 |
| 7 | (−) chr 1: 154420719-154426128 | x | −2.9 |
| 8 | (+) chr 2: 231973667-231981798 | | −2.8 |
| 9 | (+) chr 2: 188084458-188084785 | x | −2.7 |
| 10 | (+) chr 6: 131658190-131664031 | x | −2.7 |
| 11 | (+) chr 2: 201711970-201712935 | | −2.7 |
| 12 | (−) chr 6: 82110364-82117596 | x | −2.7 |
| 13 | (+) chr 7: 93107183-93112802 | | 2.6 |
| 14 | (+) chr 6: 2833115-2833223 | | −2.5 |
| 15 | (−) chr 2: 71238414-71246247 | | −2.5 |
| 16 | (−) chr 17: 38571826-38572147 | | 2.5 |
| 17 | (+) chr 3: 133508751-133509387 | | −2.4 |
| 18 | (+) chr 20: 24856581-24861663 | | −2.4 |
| 19 | (+) chr 13: 108715439-108721465 | | −2.4 |
| 20 | (+) chr 7: 17420212-17426910 | x | −2.3 |
| 21 | (−) chr 2: 54587807-54590183 | | −2.3 |
| 22 | (−) chr 11: 49820917-49821387 | | −2.2 |
| 23 | (−) chr 1: 79726879-79732396 | | −2.2 |
| 24 | (−) chr 20: 15911118-15913833 | | 2.2 |
| 25 | (+) chr X: 93632019-93639453 | x | −2.2 |
| 26 | (−) chr 2: 58194071-58199769 | | 2.1 |
| 27 | (−) chr 1: 176376976-176378817 | | −2.1 |
| 28 | (−) chr 13: 112501931-112502014 | | −2.0 |
| 29 | (+) chr 3: 95139589-95145594 | | −2.0 |
| 30 | (−) chr 6: 27901601-27902447 | | 2.0 |
| 31 | (+) chr 8: 86591572-86592049 | | −2.0 |
| 32 | (+) chr 16: 55266229-55266680 | | 2.0 |
| 33 | (−) chr 2: 165222667-165224367 | | −2.0 |
| 34 | (+) chr 6: 152853219-152859441 | | −2.0 |
| 35 | (+) chr 6: 111558919-111565969 | | −1.9 |
| 36 | (+) chr 11: 73926652-73927082 | | −1.9 |
| 37 | (−) chr 19: 51297295-51305072 | | 1.9 |
| 38 | (−) chr 8: 138907724-138911942 | | −1.9 |
| 39 | (−) chr 1: 144779633-144780605 | | 1.9 |
| 40 | (−) chr 6: 32732881-32733838 | x | −1.9 |

TABLE-continued

| SEQ ID NO: | Chromosomal location | Target tissue | Cancer/normal expression ratio |
|---|---|---|---|
| 41 | (−) chr 1: 144779633-144780605 | | 1.9 |
| 42 | (−) chr 3: 130037918-130043560 | | −1.8 |
| 43 | (−) chr Y: 13388258-13388740 | | 1.8 |
| 44 | (+) chr 9: 34993290-34999333 | | −1.8 |
| 45 | (−) chr 12: 84386849-84387812 | | −1.8 |
| 46 | (+) chr 1: 13551727-13561236 | | −1.7 |
| 47 | (−) chr Y: 21547357-21548314 | | −1.7 |
| 48 | (+) chr 15: 49439487-49440297 | | −1.7 |
| 49 | (+) chr 2: 30592323-30596634 | | 1.7 |
| 50 | (+) chr 14: 73239795-73245370 | | −1.7 |
| 51 | (−) chr 12: 11656097-11659027 | | −1.7 |
| 52 | (−) chr 19: 46119961-46120936 | | −1.7 |
| 53 | (+) chr 17: 75988189-75996283 | | −1.7 |
| 54 | (+) chr 1: 204107496-204110550 | | −1.7 |
| 55 | (−) chr 1: 223094264-223100407 | | 1.7 |
| 56 | (−) chr 1: 89419377-89419778 | | −1.7 |
| 57 | (+) chr 7: 122244019-122250290 | | −1.7 |
| 58 | (+) chr 2: 231645891-231645949 | | 1.7 |
| 59 | (+) chr 1: 201726731-201727141 | | −1.6 |
| 60 | (−) chr 1: 12762845-12768665 | | −1.6 |
| 61 | (−) chr 1: 196365449-196366430 | | −1.6 |
| 62 | (−) chr 5: 170360805-170364300 | | −1.6 |
| 63 | (+) chr 11: 76938868-76944155 | | −1.6 |
| 64 | (−) chr 18: 64760486-64761450 | | −1.6 |
| 65 | (+) chr 7: 76807190-76813131 | | −1.6 |
| 66 | (−) chr 7: 128961001-128961758 | | −1.6 |
| 67 | (−) chr 16: 69214387-69217522 | | −1.6 |
| 68 | (−) chr 17: 59750387-59751101 | | −1.5 |
| 69 | (+) chr 19: 45269688-45270401 | | 1.5 |
| 70 | (+) chr 14: 22268133-22268207 | | −1.5 |
| 71 | (+) chr 10: 55596442-55602269 | | −1.5 |
| 72 | (+) chr 13: 55512386-55518412 | | −1.5 |
| 73 | (+) chr 19: 57816195-57826383 | | 1.5 |
| 74 | (−) chr 14: 24964620-24969975 | | −1.5 |
| 75 | (+) chr 7: 125337255-125351402 | | −1.5 |
| 76 | (−) chr 1: 171684177-171684627 | | −1.5 |
| 77 | (+) chr 13: 35788462-35794330 | | −1.5 |
| 78 | (−) chr 5: 143285967-143286088 | | 1.5 |
| 79 | (+) chr 18: 13646676-13647837 | | 1.5 |
| 80 | (−) chr 19: 60210007-60215603 | | −1.5 |
| 81 | (−) chr 4: 4052713-4058389 | | −1.5 |
| 82 | (−) chr 2: 62312529-62318338 | | −1.5 |
| 83 | (+) chr 3: 147554294-147559942 | | −1.5 |
| 84 | (−) chr 13: 60755266-60755331 | | −1.5 |
| 85 | (−) chr 15: 65048616-65056011 | | 1.5 |
| 86 | (−) chr 4: 4030945-4038383 | | −1.5 |
| 87 | (+) chr 13: 27913017-27913666 | | −1.5 |
| 88 | (+) chr 14: 101776047-101781857 | | 1.5 |
| 89 | (−) chr 5: 95528434-95530534 | | 1.4 |
| 90 | (−) chr 15: 85890568-85891324 | | −1.4 |
| 91 | (−) chr 6: 68639470-68641070 | | −1.4 |
| 92 | (+) chr 6: 63353796-63359590 | | −1.4 |
| 93 | (+) chr 6: 91950297-91950513 | | 1.4 |
| 94 | (−) chr 19: 20721466-20730278 | | −1.4 |
| 95 | (+) chr 16: 10506850-10507201 | | −1.4 |
| 96 | (+) chr 1: 146832410-146833382 | | 1.4 |
| 97 | (+) chr 8: 24149948-24150249 | | 1.4 |
| 98 | (+) chr 2: 34773168-34775448 | | −1.4 |
| 99 | (−) chr 11: 23865384-23871043 | | −1.4 |
| 100 | (+) chr 8: 98282174-98288062 | | 1.4 |
| 101 | (+) chr 19: 19756756-19757058 | | 1.4 |
| 102 | (−) chr 4: 135818540-135824157 | | −1.4 |
| 103 | (+) chr 3: 184711418-184714409 | | −1.4 |
| 104 | (+) chr 3: 75269085-75276706 | | 1.4 |
| 105 | (+) chr 2: 71468737-71476455 | | −1.4 |
| 106 | (−) chr 9: 73768007-73768097 | | −1.4 |
| 107 | (+) chr 5: 111807288-111815094 | | −1.4 |
| 108 | (+) chr 17: 70760297-70765658 | | 1.4 |
| 109 | (−) chr 6: 16064468-16065182 | | −1.4 |
| 110 | (+) chr 1: 4781688-4782412 | | −1.4 |
| 111 | (−) chr 16: 58106314-58114369 | | −1.4 |
| 112 | (+) chr 8: 91057690-91058157 | | 1.4 |
| 113 | (+) chr 2: 215375861-215376821 | | 1.4 |
| 114 | (−) chr 12: 17764451-17768938 | | 1.4 |
| 115 | (−) chr X: 112238600-112244308 | | −1.4 |
| 116 | (−) chr 5: 92818136-92819135 | | −1.4 |
| 117 | (−) chr 1: 79877033-79882760 | | −1.4 |
| 118 | (−) chr 4: 95433460-95438743 | | −1.4 |
| 119 | (+) chr 16: 29617077-29617563 | | −1.4 |
| 120 | (−) chr 5: 121980485-121987968 | | −1.4 |
| 121 | (−) chr 13: 55050362-55056223 | | 1.4 |
| 122 | (+) chr 18: 31049990-31056476 | | −1.4 |
| 123 | (−) chr X: 73258716-73266192 | | −1.3 |
| 124 | (+) chr 5: 55618832-55619003 | | −1.3 |
| 125 | (+) chr 3: 156178559-156179784 | | 1.3 |
| 126 | (−) chr 3: 45334152-45335128 | | 1.3 |
| 127 | (−) chr 5: 100347893-100353827 | | 1.3 |
| 128 | (−) chr 6: 161967666-161968129 | | 1.3 |
| 129 | (−) chr 21: 20291919-20292024 | | −1.3 |
| 130 | (−) chr 11: 3451335-3458971 | | −1.3 |
| 131 | (+) chr 8: 105367316-105373215 | | 1.3 |
| 132 | (+) chr 18: 2829330-2829995 | | −1.3 |
| 133 | (−) chr 13: 90298826-90304533 | | −1.3 |
| 134 | (−) chr 3: 180722967-180726830 | | −1.3 |
| 135 | (−) chr 8: 129693327-129699058 | | −1.3 |
| 136 | (+) chr 5: 5852293-5852397 | | 1.3 |
| 137 | (−) chr 6: 122854248-122854377 | | 1.3 |
| 138 | (−) chr 7: 5033421-5033757 | | 1.3 |
| 139 | (+) chr 6: 130555149-130561062 | | −1.3 |
| 140 | (+) chr 12: 94666771-94672799 | | −1.3 |
| 141 | (−) chr 9: 29178033-29178600 | | 1.3 |
| 142 | (+) chr 11: 40847438-40848141 | | −1.3 |
| 143 | (+) chr 11: 321893-322552 | | −1.3 |
| 144 | (−) chr 4: 167866387-167867014 | | −1.3 |
| 145 | (−) chr 1: 220215255-220218922 | | −1.3 |
| 146 | (−) chr 22: 37122490-37122813 | | −1.3 |
| 147 | (−) chr 2: 80956433-80960797 | | 1.3 |
| 148 | (+) chr 6: 63559535-63565316 | | −1.3 |
| 149 | (−) chr 18: 3013633-3013763 | | −1.3 |
| 150 | (−) chr 12: 20983776-20984452 | | 1.3 |
| 151 | (+) chr 6: 142192789-142193227 | | −1.3 |
| 152 | (+) chr 6: 125253252-125260608 | | 1.3 |
| 153 | (+) chr 4: 175540733-175541728 | | −1.3 |
| 154 | (−) chr 10: 65826993-65827758 | | −1.3 |
| 155 | (−) chr 8: 12395268-12398823 | | −1.3 |
| 156 | (+) chr 13: 61603944-61604298 | | 1.3 |
| 157 | (−) chr 3: 178866314-178871614 | | 1.3 |
| 158 | (−) chr 12: 20862483-2086818 | | −1.3 |
| 159 | (−) chr 10: 59523861-59524645 | | 1.3 |
| 160 | (−) chr 7: 79651365-79652053 | | 1.3 |
| 161 | (−) chr 11: 69581214-69582655 | | −1.3 |
| 162 | (+) chr 21: 44461476-44462142 | | 1.3 |
| 163 | (−) chr 2: 105967906-105968229 | | 1.3 |
| 164 | (+) chr 6: 123199111-123199590 | | 1.3 |
| 165 | (+) chr 9: 22813029-2281338 | | −1.3 |
| 166 | (−) chr 14: 41740538-41741242 | | 1.3 |
| 167 | (−) chr 18: 1990815-1991782 | | 1.3 |
| 168 | (+) chr 3: 8686697-8686961 | | −1.3 |
| 169 | (−) chr 2: 38161446-38167158 | | −1.3 |
| 170 | (−) chr 10: 101570559-101571639 | | 1.3 |
| 171 | (−) chr 15: 31130887-31131553 | | −1.3 |
| 172 | (+) chr 7: 65695119-65695525 | | −1.3 |
| 173 | (−) chr 8: 828875-829287 | | 1.3 |
| 174 | (+) chr 6: 160569673-160575346 | | −1.3 |
| 175 | (−) chr 10: 53463521-53469342 | | −1.3 |
| 176 | (−) chr 4: 176619310-176625331 | | 1.3 |
| 177 | (+) chr 12: 122598918-122609265 | | 1.3 |
| 178 | (−) chr 3: 78475709-78476509 | | −1.3 |
| 179 | (−) chr X: 37202604-37205422 | | −1.3 |
| 180 | (−) chr 1: 23196587-23203483 | | −1.2 |
| 181 | (+) chr 18: 38295804-38303710 | | −1.2 |
| 182 | (+) chr 4: 54581003-54585874 | | −1.2 |
| 183 | (+) chr 9: 35630300-35632824 | | 1.2 |
| 184 | (−) chr X: 8364892-8365592 | | 1.2 |
| 185 | (−) chr 6: 24784895-24791307 | | −1.2 |
| 186 | (−) chr 14: 79937761-79938478 | | −1.2 |
| 187 | (+) chr 2: 142963716-142969364 | | −1.2 |
| 188 | (+) chr X: 30031651-30037293 | | 1.2 |
| 189 | (+) chr 2: 63928103-63928550 | | 1.2 |
| 190 | (+) chr X: 92571323-92580146 | | −1.2 |
| 191 | (+) chr 7: 100353142-100354585 | | 1.2 |
| 192 | (+) chr 9: 113677404-113678370 | | −1.2 |

TABLE-continued

| SEQ ID NO: | Chromosomal location | Target tissue | Cancer/normal expression ratio |
|---|---|---|---|
| 193 | (+) chr 9: 129215427-129217168 | | -1.2 |
| 194 | (+) chr 4: 171274156-171279886 | | -1.2 |
| 195 | (-) chr 2: 52103626-52108242 | | -1.2 |
| 196 | (-) chr 2: 16846720-16847190 | | 1.2 |
| 197 | (+) chr 3: 187581597-187582311 | | -1.2 |
| 198 | (-) chr 12: 77758546-77759251 | | 1.2 |
| 199 | (-) chr 20: 740491-741481 | | 1.2 |
| 200 | (-) chr 3: 21205514-21210699 | | 1.2 |
| 201 | (-) chr 15: 49734758-49735530 | | -1.2 |
| 202 | (-) chr 3: 103933971-103934748 | | -1.2 |
| 203 | (-) chr 4: 177452380-177455182 | | 1.2 |
| 204 | (-) chr 9: 75103859-75104219 | | -1.2 |
| 205 | (+) chr 1: 237334832-237336987 | | -1.2 |
| 206 | (-) chr 13: 55584544-55586741 | | 1.2 |
| 207 | (-) chr 12: 29178820-29185001 | | -1.2 |
| 208 | (-) chr 20: 36760391-36760718 | | 1.2 |
| 209 | (+) chr 20: 32476466-32477455 | | 1.2 |
| 210 | (+) chr 4: 8492255-8492953 | | -1.2 |
| 211 | (+) chr 10: 65936583-65936972 | | 1.2 |
| 212 | (+) chr 11: 22761631-22761856 | | 1.2 |
| 213 | (+) chr 9: 133412422-133417146 | | -1.2 |
| 214 | (-) chr 4: 41854992-41855740 | | 1.2 |
| 215 | (+) chr 12: 60267154-60272981 | | -1.2 |
| 216 | (-) chr 3: 32477433-32480101 | | -1.2 |
| 217 | (+) chr 18: 70111304-70117249 | | -1.2 |
| 218 | (+) chr 19: 58554156-58559856 | | -1.2 |
| 219 | (+) chr X: 53557364-53557692 | | 1.2 |
| 220 | (-) chr 5: 34514678-34514916 | | -1.2 |
| 221 | (+) chr 6: 26107438-26108404 | | 1.2 |
| 222 | (-) chr 10: 6906147-6915609 | | 1.2 |
| 223 | (+) chr 1: 89162808-89170138 | | -1.2 |
| 224 | (+) chr 5: 741636041-74638012 | | 1.2 |
| 225 | (-) chr 5: 115707988-115708051 | | -1.2 |
| 226 | (-) chr X: 72938020-72941188 | | -1.1 |
| 227 | (+) chr Y: 26648032-26648192 | | 1.1 |
| 228 | (+) chr 18: 6123610-6123972 | | 1.1 |
| 229 | (-) chr 3: 110377937-110378340 | | -1.1 |
| 230 | (-) chr 9: 101942283-101948625 | | -1.1 |
| 231 | (+) chr 10: 100097920-100098685 | | 1.1 |
| 232 | (-) chr 4: 135768442-135768594 | | 1.1 |
| 233 | (+) chr 11: 18656991-18657966 | | 1.1 |
| 234 | (-) chr 7: 68382377-68383085 | | 1.1 |
| 235 | (-) chr X: 85929452-85930118 | | -1.1 |
| 236 | (+) chr 4: 1992875-1993855 | | -1.1 |
| 237 | (+) chr 5: 64505763-64506756 | | 1.1 |
| 238 | (+) chr 18: 8944363-8944760 | | 1.1 |
| 239 | (-) chr 1: 225849586-225850738 | | -1.1 |
| 240 | (+) chr 2: 199752333-199758641 | | -1.1 |
| 241 | (-) chr X: 137174181-137180160 | | -1.1 |
| 242 | (+) chr 9: 12938344-12944129 | | -1.1 |

The subject of the present invention is therefore a method for the in vitro diagnosis of lung cancer or for the in vitro prognosis of the seriousness of lung cancer in a biological sample taken from a patient, which comprises detecting at least one expression product of at least one nucleic acid sequence, said nucleic acid sequence being chosen from the full-length sequences identified in SEQ ID NOs: 1 to 242 or from the sequences which exhibit at least 99% identity, preferably at least 99.5% identity and advantageously at least 99.6% or at least 99.7% identity with one of the full-length sequences identified in SEQ ID NOs: 1 to 242.

The diagnosis makes it possible so establish whether or not an individual is ill. The prognosis makes it possible to establish a degree of seriousness of the disease (grades and/or stages) which has an effect on the survival and/or quality of life of the individual. In the context of the present invention, the diagnosis may be very early.

The percentage identity described above has beer; determined by taking into consideration the nucleotide diversity in the genome. It it is known chat nucleotide diversity is higher in regions or the genome that are rich in repeat sequences than in regions which do not contain repeat sequences. By way of example, Nickerson D. A. et al. (1) have shown a diversity of approximately 0.3% (0.32%) in. regions containing repeat sequences.

The ability to discriminate, a cancerous state of each of the sequences identified above has been demonstrated by evens of a statistical analysis using the SAM procedure (5), followed by correction by means oil the rate of false positives (6) and by elimination of the values below 2'. Consequently, each of the sequences identified above exhibits a significant difference in expression between a tumor state and a normal state. As a result oil this, a difference in expression observed for one of the above-mentioned sequences constitutes a signature of the pathological condition. Of coarse, it is possible to combine the differences in express ion noted for several of the sequences referenced above for example by one or snore combinations of 2, 3, 4, 5, 6, 7, 8, 9, 10 and more, or even up to 242 of the listed sequences. In particular:, the sequences identified in SEQ ID NOs: 1, 6 and 50, taken alone or in combination (in pairs or all three) constitute one or core preferred signatures.

Thus, in the tithed of the invention, at least two expression products respectively of at least two nucleic and, sequences are detected, said nucleic acid sequences being chosen from the sequences identified in SEQ ID NOs: 1 to 242 and in particular chosen from the sequences identified in SEQ ID NOs: 1, 6 and 50 or frost the sequences which exhibit au least 90% identity, preferably at least 99.52 identity and advantageously at least 99.6% or at least 99.7% identity with one of the abovementioned identified sequences.

In one embodiment of the method according to the invention, the expression product of at least two nucleic acid sequences is detected, said at least two nucleic acid sequences being chosen from the sequences identified as being specific for lung tissue, i.e. chosen from the group of sequences identified in SEQ ID NOs: 4, 5, 7, 9, 10, 12, 20, 25 and 40, in particular chosen from the .sequences identified in SEQ ID NOs 4, 5 and 7 or from the sequences which exhibit at least 99% identity, preferably at least 90.5% identity and advantageously at least 99.6% or at least 99.7% identity with One of the sequences identified in SEQ ID NOs: 4, 5, 7, 9, 10, 12, 20, 25 and 40 and in particular those which exhibit at least 99% identity, preferably at least 99.5% identity and advantageously at least 99.6% or at least 99.7% identity with one of the sequences identified in SEQ ID NOs: 4, 5 and 7.

In another embodiment of the method of the invention, the expression product of at least two nucleic acid sequences chosen from the sequences identified as being not specific for lung tissue, i.e. chosen from the group of sequences identified in SEQ ID NOs: 1, 2, 3, 6, 8, 11, 13, 14, 15, 16, 17, 18, 19, 21, 22, 23, 24, 26, 27, 28, 29, 30, 31, 32, 33, 34, 33, 36, 37, 38, 39, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 153, 159, 160, 161, 162, 163, 164, 165, 166, 167, 168, 169, 170, 171, 172, 173, 174, 175, 176, 177, 178, 179, 181, 162, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 252, 233, 234, 235, 236, 237, 238, 239, 240, 241 and 242, in particular the sequences chosen from the sequences identified in SEQ ID NOs: 1, 6 and 50 or chosen from the sequences which exhibit at least 99% identity, preferably at least 99.51 identity and advantageously at least 99.6% or at least 99.7% identity with one of the sequences identified in SEQ ID NOs: 1, 2, 3, 6, 8, 11, 13, 14, 15, 16, 17, 18, 19, 21, 22, 23, 24, 26, 27, 28, 29, 30, 31, 32, 33, 34, 35, 36, 37, 38, 39, 41, 42, 43, 44, 45, 46, 47, 48, 49, 50, 51, 52, 53, 54, 55, 56, 57, 38, 59, 60, 61, 62, 63, 64, 65, 66, 67, 68, 69, 70, 71, 72, 73, 74, 75, 76, 77, 78, 79, 80, 81, 82, 83, 84, 85, 86, 37, 88, 89, 90, 91, 92, 93, 94, 95, 96, 97, 98, 99, 100, 191, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 187, 138, 130, 140, 141, 142, 143, 144, 145, 146, 147, 148, 149, 150, 151, 152, 153, 154, 155, 156, 157, 158, 159, 160, 161, 162, 163, 164, 165, 166, 167, 163, 169, 170, 171, 172, 173, 174, 175, 176, 177, 178, 179, 180, 181, 182, 183, 184, 185, 186, 187, 188, 189, 190, 191, 192, 193, 194, 195, 196, 197, 196, 199, 200, 201, 202, 203, 204, 203, 206, 207, 208, 209, 210, 211, 212, 213, 214, 215, 216, 217, 218, 213, 220, 221, 222, 223, 224, 225, 226, 227, 228, 229, 230, 231, 232, 233, 234, 233, 233, 237, 238, 239, 240, 241 and 242, and in particular from the sequences which exhibit at least 99.5% identity and advantageously at least 99.6% or at least 99.7% identity with one of the sequences identified in SEQ ID NOs: 1, 6 and 50, is detected.

In yet another embodiment of the invention, the expression product of at least one sequence chosen from the sequences identified as being specific for lung tissue, i.e. chosen from the group of sequences; identified in SEQ ID NOs: 4, 3, 7, 3, 10, 12, 20, 25 and 40, in particular chosen from the sequences identified in SEQ ID NOs: 4, 5 and 7 and the sequences which exhibit at least 99.5% identity and advantageously at least 99.6% or at least 95.7% identity with one of the sequences above (i.e. the variants of said sequences) and at least one sequence chosen frosts the sequences identified as being not specific for lung tissue, i.e. the sequences identified in SEQ ID NOs: 1, 2, 3, 6, 8, 11, 13, 14, 15, 16, 17, 18, 19, 21, 22, 23, 24, 26, 27, 28, 29, 30, 31, 32, 33, 34, 35, 36, 37, 38, 39, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 135, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241 and 242, in particular the sequences identified in SEQ ID NOs: 1, 6 and 50 and their variants as defined above, is detected.

Preferably, in the method of the invention, the expression product of at least one nucleic acid sequence, preferably of at least two nucleic acid sequences or of three nucleic acid sequences is detected, said nucleic acid sequences being chosen from the group of sequences identified in SEQ ID NOs: 1, 6 and 50, or from the sequences which exhibit at least 99% identity, preferably at least 99.5% identity and advantageously at least 99.6% or at least 99.7% identity with the sequences identified in SEQ ID NOs: 1, 6 and 50.

The expression product detected is at least one RNA transcript, in particular at least one mRNA or at least one polypeptide.

When the expression product is an mRNA transcript, it is detected by any appropriate method, such as hybridization, sequencing or amplification. The mRNA may be detected directly by bringing into contact with at least one probe and/or at least one primer which are designed so as to hybridize to the mRNA transcripts under predetermined experimental conditions, demonstrating the presence or the absence of hybridization to the mRNA and optionally quantifying the mRNA. Among the preferred methods, mention may be made of amplification (for example, RT-PCR, NSBA, etc), hybridization on a chip or else sequencing. The mRNA may also be detected indirectly using nucleic acids derived from said transcripts, such as cDNA copies, etc.

Generally, the method of the invention comprises an initial step of extracting the mRNA from the sample to be analyzed.

Thus, the method may comprise:

(i) a step of extracting the mRNA from the sample to be analyzed, (ii) a step of detecting and quantifying the mRNA from the sample to be analyzed, (iii) a step of extracting the mRNA in a reference sample, which may be a healthy sample originating in the same individual, or (iv) a step of detecting and quantifying the mRNA from the healthy samples, (v) a step of comparing the amount of mRNA expressed in the sample to be analyzed and in the reference sample; it being possible for the determination of an amount of mRNA expressed in the sample to be analyzed which is different than the amount of mRNA expressed in the healthy reference sample to be correlated with the diagnosis or the prognosis of the seriousness of lung cancer (the difference in the amount of mRNA in the cancerous lung tissue relative to the amount of mRNA expressed in the healthy lung tissue being indifferently an expression, an overexpression or an underexpression);

and in particular:

(i) an extraction of the mRNA to be analyzed from the sample, (ii) a determination, in the RNA to be analyzed, of an expression level of at least one RNA sequence in the sample, said RNA sequence being the transcription product of at least one nucleic acid sequence chosen from the sequences identified in SEQ ID NOs: 1 to 292 or from the sequences which exhibit at least 92% identity, preferably at least 99.5% identity and advantageously at least 99.6% or at least 99.7% identity with one of the sequences identified in SEQ ID NOs: 1 to 242, and (iii) a comparison of the expression level of the RNA sequence(s) defined in (ii) with a reference expression level; it being possible for the determination of an expression level of the RNA to be analyzed which exhibits a difference relative to the reference expression level to be correlated with the diagnosis or the prognosis of lung cancer (as determined above); or (i) a step of extracting the mRNA from the sample to be analyzed, (ii) a step of detecting and quantifying the mRNA from the sample to be analyzed, (iii) a step of comparing the amount of mRNA expressed in the sample to be analyzed relative to an amount of reference mRNA, it being possible for the determination of an amount of mRNA expressed in the sample to be analyzed which is different than the amount of reference mRNA to be correlated with the diagnosis or the prognosis of lung cancer (the difference in the amount of mRNA in the sample to be analyzed relative to the amount of reference mRNA being indifferently an expression, an overexpression or an underexpression).

In one embodiment of the method of the invention, DNA copies of the mRNA are prepared, the DNA copies are brought into contact with at least one probe and/or at least one primer under predetermined conditions which allow hybridization, and the presence or absence of hybridization to said DNA copies is detected.

The expression product which is detected may also be a polypeptide which is the translation product of at least one of the transcripts described above. In this case, the polypeptide expressed is detected by bringing into contact with at least one specific binding partner of said polypeptide, in particular an antibody or an antibody analog or an aptamer. The binding partner is preferably an antibody, for example a monoclonal antibody or a polyclonal antibody which is highly purified or an antibody analog, for example an affinity protein with competitive properties (nanofitin™).

The polyclonal antibodies can be obtained by immunization of an animal with the appropriate immunogen, followed by recovery of the desired antibodies in purified form, by taking the serum of said animal, and separation of said antibodies from the other serum constituents, in particular by affinity chromatography on a column to which an antibody specifically recognized by the antibodies is bound.

The monoclonal antibodies can be obtained by means of the hybridoma technology, the general principle of which is summarized below.

Firstly, an animal, generally a mouse, is immunized with the appropriate immunogen, and the B lymphocytes of said mouse are then capable oil producing antibodies against this antigen. These antibody-producing lymphocytes are then infused with "immortal" myeloma cells (murine in the example) so as to give rise to hybridomas. The cells capable of producing a particular antibody and of multiplying indefinitely are then selected from the heterogeneous mixture oil cells thus obtained, each hybridoma is multiplied in the forms of a clone, each one resulting in the production of a monoclonal antibody in which the properties of recognition with respect to the protein may be tested, for example, by ELISA, by one-dimensional or two-dimensional Western blotting, by immunofluorescence, or using a biosensor. The monoclonal antibodies thus selected are subsequently purified, in particular according to the affinity chromatography technique described above.

The monoclonal antibodies may also be recombinant antibodies obtained by genetic engineering, using techniques well known to those skilled in the art.

Nanofitins™ are small proteins which, like antibodies, are capable of binding to a biological target, thus mating it possible to detect it, to capture it or quite simply to target it within an organism. They are presented, inter alia, as antibody analogs.

Aptamers are synthetic oligonucleotides capable of binding a specific ligand.

The invention also relates to the use of at least one nucleic acid sequence, once isolated, as a molecular marker for the in vitro diagnosis or prognosis of lung cancer, characterized in that said nucleic acid sequence consists of:

(i) at least one DNA sequence chosen from the sequences SEQ ID NOs: 1 to 242, or (ii) at least cue DNA sequence complementary to a sequence chosen from the sequences SEQ ID NOs: 1 to 242, or (iii) at least one DNA sequence which exhibits at least 99% identity, preferably at least 99.5% identity and advantageously at least 99.6% or at least 99.7% identity with a sequence as defined in (i) and (ii), or (iv) at least one DNA sequence which is the transcription product of a sequence chosen from the sequences as defined in (i), or (v) at least one RNA sequence which is the transcription product of a sequence chosen from the sequences which exhibit at least 99% identity, preferably at least 99.5% identity and advantageously at least 99.6% or at least 99.7% identity with a sequence as defined in (i).

In one embodiment, use is made of at least two nucleic acid sequences which consist of:

(i) at least two DNA sequences chosen from the sequences SEQ ID NOs: 1 to 242, preferably chosen from the sequences identified in SEQ ID NOs: 1, 2, 3, 6, 8, 11, 13, 14, 15, 16, 17, 18, 19, 21, 22, 23, 24, 26, 27, 28, 29, 30, 31, 32, 33, 34, 35, 36, 37, 38, 39, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 80, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 178, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 232, 234, 235, 236, 237, 238, 239, 240, 241 and 242 or their variants, in particular from the sequences identified in SEQ ID NOs: 1, 6 and 50 or their variants as defined above, or at least two sequences chosen from the sequences identified in SEQ ID NOs: 4, 5, 7, 9, 10, 12, 20, 25 and 40, in particular chosen from the sequences identified in SEQ ID NOs: 4, 5 and 7 or their variants as defined above, or else at least one DNA sequence chosen from the sequences identified in SEQ ID NOs: 1, 2, 3, 6, 8, 11, 13, 14, 15, 16, 17, 18, 19, 21, 22, 23, 24, 26, 27, 28, 29, 30, 31, 32, 33, 34, 35, 36, 37, 38, 39, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241 and 242 or their variants, in particular chosen from the sequences identified in SEQ ID NOs: 1, 6 and 50 or their variants as defined above and at least one sequence chosen from the sequences identified in SEQ ID NOs: 4, 5, 7, 9, 10, 12, 20, 25 and 40, in particular chosen from the sequences identified in SEQ ID NOs: 4, 5 and 7 or their variants as defined above, or (ii) at least two DNA sequences respectively complementary to at least two sequences chosen from at least two sequences as defined in (i), or (iii) at least two DNA sequences which exhibit respectively at least 99% identity, preferably at least 99.5% identity and advantageously at least 99.6% or at least 99.7% identity with two sequences as defined in (i) and (ii), or (iv) at least two RNA sequences which are respectively the transcription product of two sequences chosen from the sequences as defined in (i), or (v) at least two RNA sequences which are the transcription product of two sequences chosen from the sequences which exhibit at least 99% identity, preferably at least 99.5% identity and advantageously at least 99.6% or at least 99.7% identify with the sequences as defined in (i).

A subject of the invention is also a kit for the in vitro diagnosis or prognosis of lung cancer in a biological sample taken from a patient, which comprises at least one specific binding partner of at least, one expression product, of at least, one nucleic acid sequence chosen from the sequences identified in SEQ ID NOs: 1 to 242 or from the sequences which exhibit at least 99% identity, preferably at least 99.5% identity, advantageously at least 99.6% or at least 99.7% identity with the nucleic acid sequences identified in SEQ ID NOs: 1 to 242 and no more than 242 specific binding partners of the expression products of the nucleic amid sequences identified in SEQ ID NOs: 1 to 242 or of the nucleic acid sequences which exhibit at least 99% identity with the nucleic acid sequences identified in SEQ ID NOs: 1 to 242, preferably at least 99.5% identity and advantageously at least 99.6% or at least 99.7% identity with one of the sequences identified in SEQ ID NOs: 1 to 242.

In one embodiment, the kit comprises at least two respectively specific binding partners of at least two expression products of at least two nucleic acid sequences chosen from the sequences identified in SEQ ID NOs: 1 to 242 or from the sequences which exhibit at lease: 99% identity, preferably at least 99.5% identity and advantageously at least 99.6% or at least 99.7% identity with the nucleic acid sequences identified in SEQ ID NOs: 1 to 242 and no more than 242 specific binding partners of the expression products of the nucleic acre sequences identified in SEQ ID NOs: 1 to 242 or of the nucleic acid sequences which exhibit at least 99% identity, preferably at least 99.5% identity and advantageously at least 99.6% or at least 99.7% identity with the nucleic acid sequences identified in SEQ ID NOs: 1 to 242.

For example, the kit comprises at least two respectively specific binding partners of the expression product of at least two nucleic acid sequences chosen from:

(i) the group of sequences identified in. SEQ ID NOs: 1, 2, 3, 6, 8, 11, 13, 14, 15, 16, 17, 18, 19, 21, 22, 23, 24, 26, 27, 28, 29, 30, 31, 32, 33, 34, 35, 36, 37, 38, 39, 41, 42, 43, 44, 45, 46, 47, 48, 49, 50, 51, 52, 53, 54, 55, 56, 57, 58, 59, 60, 61, 62, 68, 64, 65, 66, 67, 68, 69, 70, 71, 72, 73, 74, 75, 76, 77, 76, 70, 80, 81, 32, 83, 84, 65, 86, 87, 88, 89, 90, 91, 92, 93, 94, 95, 96, 97, 98, 99, 100, 101, 102, 103, 104, 105, 106, 107, 108, 103, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 143, 146, 147, 148, 149, 150, 151, 152, 153, 154, 155, 156, 157, 138, 159, 160, 161, 162, 163, 164, 165, 166, 167, 166, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 210, 220, 221, 222, 223, 224, 225, 226, 227, 228, 229, 230, 231, 232, 233, 234, 235, 236, 237, 238, 239, 240, 241 and 242, in particular chosen from, the sequences identified in SEQ ID NOs: 1, 6 and 50.

(ii) the group of sequences identified in SEQ ID NOs: 4, 5, 7, 9, 10, 12, 20, 25 and 40, in particular the sequences identified in SEQ ID NOs: 4, 5 and 7, (iii) from, the group of sequences consisting of at least one DNA sequence chosen front the sequences identified in SEQ ID NOs: 1, 2, 3, 6, 8, 11, 13, 14, 15, 16, 17, 18, 19, 21, 22, 23, 24, 26, 27, 28, 29, 30, 31, 32, 33, 34, 35, 36, 37, 38, 39, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 136, 157, 158, 159, 160, 161, 162, 163, 164, 165, 166, 167, 168, 169, 170, 171, 172, 173, 174, 175, 176, 177, 178, 179, 180, 181, 102, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 230, 239, 240, 241 and 242, in particular chosen from the sequences identified in SEQ ID NOs: 1, 6 and 50 or the sequences which exhibit at least 99% identity with the sequences identified in SEQ ID NOs: 1, 6 and 50 and of at least one sequence chosen from the sequences identified in SEQ ID NOs: 4, 5, 7, 9, 10, 12, 20, 25 and 40 and in particular chosen from the sequences identified in SEQ ID NOs: 4, 5 and 7 or the sequences which, exhibit at least 99% identity with the sequences identified in SEQ ID NOs: 4, 5 and 7, or (iv) from the groups of sequences which, exhibit at least 99% identity, preferably at least 99.5% identity and in particular at least 99.6% or 99.7% identity with the sequences identified in the groups of sequences as described in (i), (ii) or (iii).

In particular, the kit comprises 1, 2 or 3 specific binding partner(s) of the expression product(s) of the nucleic acid sequences identified in SEQ ID NOs: 1, 6 and 50 or of the sequences which exhibit at least 99% identity, preferably at least 99.5% identity and advantageously at least 99.6% or at least 99.7% identity with, the sequences identified in SEQ ID NOs. 1, 6 and 50.

The at least specific binding partner of the expression product corresponds to the definitions given above.

The invention also relates to a method for evaluating the efficacy of a treatment and/or a progression in lung cancer, which comprises a step of obtaining a series of biological samples, and a step of detecting at least one expression product of at least one nucleic acid sequence in said series of biological carries, said nucleic acid sequence being chosen from the sequences identified in SEQ ID NOs: 1 to 242, with one of the sequences identified in SEQ ID NOs: 1 to 242 or of the sequences which exhibit at least 99% identity, preferably at least 99.5% identity and advantageously at least 99.6% or at least 99.7% identity with, the sequences identified in SEQ ID NOs: 1 to 242.

In one embodiment, at least two expression products of at least two nucleic acid sequences are detected, said two nucleic acid sequences being chosen from the sequences identified in SEQ ID NOs; 1 to 242 or frets the sequences which exhibit at least 99% identity respectively, preferably at least 99.5% identify and advantageously at least 99.6% or at least 99.7% identity with the sequences identified in SEQ ID NOs: 1 to 242.

In another embodiment of the method, the expression product of at least: one nucleic acid sequence, preferably of at least two nucleic acid sequences or of three nucleic acid sequences is detected, said nucleic acid sequences being chosen from the group of sequences identified in SEQ ID NOs: 4, 5, 7, 9, 10, 12, 20, 25 and 40 and in particular from the sequences identified in SEQ ID NOs: 4, 5 and 7 or from the sequences which exhibit at least 99% identify wish the sequences identified in SEQ ID NOs: 4, 5, 7, 9, 10, 12, 20, 25 and 40 and in particular from the sequences which exhibit at least. 99% identity with the sequences identified in SEQ ID NOs: 4, 5 and 7.

In yet another embodiment of the method of the invention, the expression product, or at least one nucleic acid sequence, preferably of at least two nucleic acid sequences or of three nucleic acid sequences is detected, said nucleic acid sequences being chosen from the group of sequences identified in SEQ ID NOs: 1, 6 and 50 or from the sequences which exhibit at least 99% identity respectively, preferably at least 99.5% identity and advantageously at least 99.6% or at least 99.7% identity with the sequences identified in SEQ ID NOs: 1, 6 and 50.

The term "biological sample" is intended to mean a tissue, a fluid, components of said tissue and fluid, such as cells or apoptotic bodies, and excreted vesicles, comprising in particular exosomes and microvesicles. By way of example, the biological, sample may be derived from a biopsy of the lung carried out beforehand in a patient suspected of suffering from lung cancer or may be derived from a biopsy carried out on an organ other than the lung in a patient presenting metastases. In this second case, when the change in expression of the nucleic acid (molecular marker) is specific for the lung organ, it is possible to work back to the primary cancer, i.e. to the lung cancer. The biological sample may also be a biological fluid, such as blood or a blood fraction (serum, plasma), urine, saliva, cerebrospinal fluid, lymph, maternal milk, sperm, and also components of said fluids, in particular excreted vesicles as defined above. For example, the detection of a transcript specific for the lung tissue in an exosome or a microvesicle, originating from an epithelial cell, is a sign of the presence either of a primary cancer or of metastases, without it being necessary to take a sample at the level of the organ.

FIGURES

FIG. 2 shows the statistical differences in expression of HERV elements between normal lung and tumoral lung.

EXAMPLES

Example 1

Identification of HERV Sequences Exhibiting Differential Expression in Lung Cancer Method:

The identification of HERV sequences exhibiting differential expression in lung cancer is based on the design, and the use of a high-density DNA chip in the GeneChip format, called HERV-V2, designed by the inventors and the fabrication of which was subcontracted to the company Affymetrix. This chip contains probes which, correspond to HERV sequences that are distinct within the human genome. These sequences were identified using a set of prototypical references cut up into functional regions (LTR, gag, pol and env), and then, by means of a similarity search on the scale of the whole human genome (NCBI 36/hg18), 10 035 distincts HERV loci were identified, annotated and finally grouped together in a databank called HERVgDB3.

The probes which are part of the composition of the chip wore defined on the basis of HERVgDB3 and selected by applying a hybridization specificity criterion, the objective of which is to exclude, from the creation process, the probes having a high risk of hybridization, with an undesired target. For this, the HERVgDB3 sequences were first segmented in sets of 25 overlapping nucleotides (25-mers), resulting in a set of candidate probes. The risk of nonspecific hybridization was then evaluated for each candidate probe by performing alignments on the whole of the human genome using the KASH algorithm (2). An experimental score marks the result of the hybridization, addition of the impact of the number, of the type and or the position of the errors in the alignment. The value of this score correlates with the target/prone hybridization potential. Knowledge of all the hybridization potentials of a candidate probe on the whole of the human genome cakes it possible to evaluate its capture specificity. The candidate probes which exhibit good capture affinity are retained and then grouped together in "probe sets" and, finally, synthesized on the HERV-V2 chip.

The samples analyzed using the HERV-V2 high-density chip correspond, to RNAs extracted from tumors and to RNAs extracted from the healthy tissues adjacent to these tumors. The tissues analyzed are the long, with breast, ovary, uterus, prostate, colon, testicle and placenta as controls. In the case of placenta, only healthy tissues were used. For each sample, 50 ng of RNA were used, for the synthesis of cDNA using the amplification protocol known as WTO. The principle of WTO amplification is the following: random primers, and also primers targeting the 3' end of the RNA transcript, are added, before a step of reverse transcription followed, by a linear, single-stranded amplification denoted SPIA. The cDNAs are then assayed, characterized in purified, and then 2 μg are fragmented, and labeled with biotin at the 3' end via the action of the terminal transferase enzyme. The target product thus prepared is mixed with control oligonucleotides, then the hybridization is carried out according to the protocol recommended by the company Affymetrix. The chips are then visualized and read in order to acquire the image of their fluorescence. A quality control based on standard controls is carried out, and a set of indicators (MAD, MAD-Med plots, RLE) serve to exclude the chips that are not in accordance with a statistical analysis.

The analysis of the chips first consists of a preprocessing of the data through the application of a correction of the background noise based on the signal intensity of tryptophan probes, followed by RMA normalization (3) based on the quantile method. A double correction of the effects linker: to the batches of experiments is then carried out by applying the COMBAT method (4) in order to guarantee that the differences in expression that are observed are of biological and not technical origin. At this stage, an exploratory analysis of the data is conducted using tools for grouping together data by Euclidean partitioning (clustering) and, finally, a statistical analysis using the SAM procedure (5) followed by a correction via the rate of false positives (6) and elimination of the values below 2° is applied in order to search for sequences exhibiting a differential expression between the normal state and the tumor state of a tissue.

Results:

The processing of the data generated by the analysis of the HERV-V2 DEA chips using this method made it possible to identify a set of "probe sets" exhibiting a statistically significant difference in expression between the normal lung and the tumoral lung. The results of the clustering and also the search for differential expression within the control samples moreover demonstrated HERV elements of which the differential expression is specifically associated with the tumoral lung.

The nucleotide sequences of the HERV elements exhibiting a differential expression in the tumoral lung are identified by SEQ ID NOs: 1 to 242, the chromosomal location, of each sequence is given in the NCBI reference 36/hg18, and the "target tissue" information (a cross) indicates the elements in which the differential expression was observed only in the comparison between normal lung and tumoral lung (compared with the comparisons within the control tissues). A value which is an indication of the ratio of expression between normal state and tumor state is also provided, and serves to order the sequences in the interests of presentation only.

Example 2

Detection of HERV Sequences in Biological Fluids

Principle:

The inventors have shown that HERV sequences are detected in biological fluids, which makes it possible, inter alia, to characterize a lung cancer through recourse to remote detection of the primary organ. A study was carried out on 20 urine samples and 38 serum samples originating from different individuals.

The sera and the urines were centrifuged under the following conditions:

Sera: 300 g for 10 minutes at 4° C. The supernatant was recovered and centrifuged again at 16 500 g for 20 minutes at 4° C.. The supernatant of this second centrifugation, devoid of cells, but also comprising exosomes, microvesicles, nucleic acids and proteins, was analyzed on chips. The chip is the HERV-V2 chip used according to the modes previously described.

Urines: after collection, centrifugation at 800 g for 4 minutes at 4° C. The pellet was recovered with RNA protect cell reagent™. Then, centrifugation at 5000 g for 5 minutes before addition of the lysis buffer to the pellet. The chip is the HERV-V2 chip used according to the modes previously described.

Figure 1:
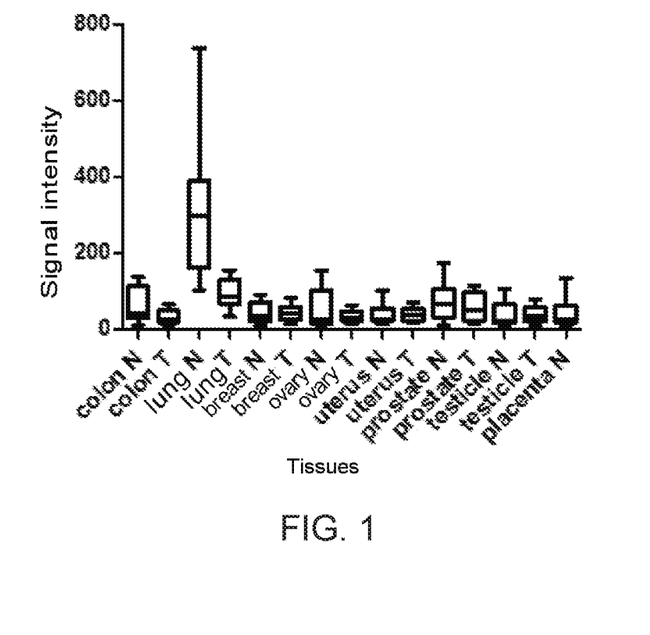
FIGS. 1 and 2 represent the differential expression observed in lung cancer for a set of HERV sequences. More specifically, FIG. 1 (clustering) groups together in an exploratory manner the HERV elements which have an expression tropism associated with the normal lung compared with ail the control tissues and cancerous tissues.
Figure 2:
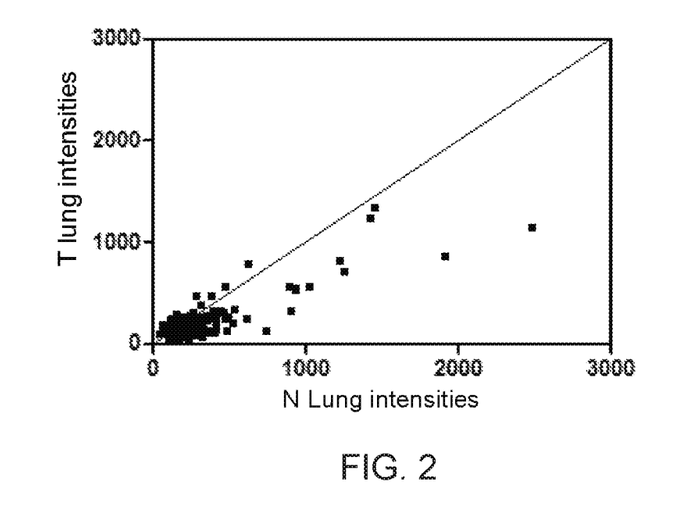
Figure 3:
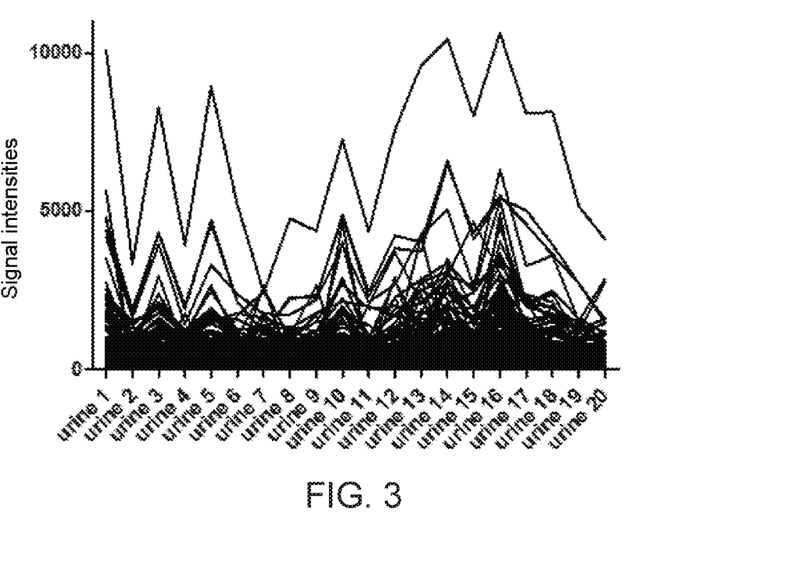
FIGS. 3 and 4 show the defection of HERV sequences in two biological fluids: urines and sera.
Figure 4:
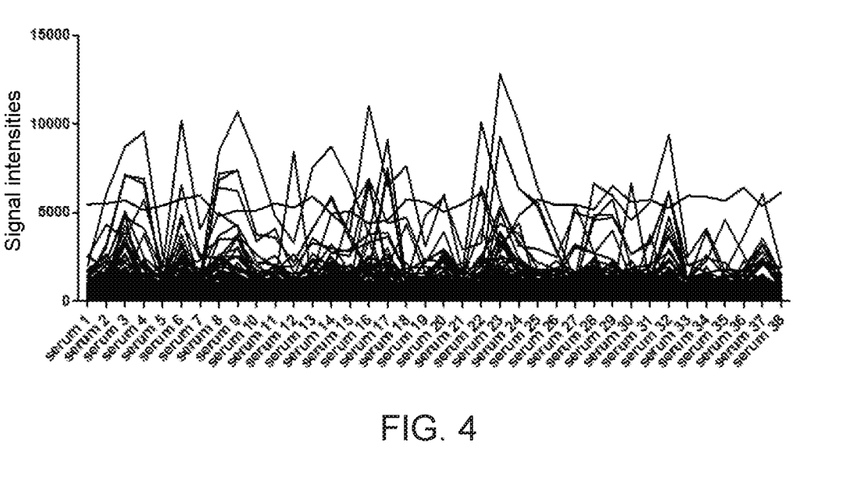

Results;

A large number of positive signals, including the expression signals corresponding to the sequences listed its the table above, was detected both in the serums supernatants and in the cell pellets originating from urines, as illustrated in figures 3 and 4, This confirms that biological fluids, in particular serum and urine, are a usable source of biological material for the detection of HERV sequences. It is commonly accepted that the positivity threshold is about 2°, i.e. 64.

LITERATURE REFERENCES

1. Nickerson, D. A., Taylor, S. L., Weiss, K. M., Clark, A. G., Hutchinson, R. G., Stengard, J., Salomaa, V., Vartiainen, E., Boerwinkle, E. and Sing, C. F. (1998) DNA sequence diversity in a 9.7-kb region of the human lipoprotein lipase gene. *Nat. Genet.*, 19, 233-240.
2. Navarro, G. and Raffinot, M. (2002) Flexible Pattern Matching in. Strings: Practical On-Line Search Algorithms for Texts and Biological Sequences. Cambridge University Press.
3. Irizarry, R. A., Hobbs, B., Collin, F., Beazer-Barclay, Y. D., Antonellis, K. J., Scherf, U. and Speed, T. P. (2003) Exploration, normalization, and summaries of high density oligonucleotide array probe level data. *Biostatistics (Oxford, England)*, 4, 249-264.
4. Johnson, W. E., Li, C. and Rabinovic, A. (2007) Adjusting batch streets in microarray expression data using empirical Bayes methods, *Biostatistics (Oxford, England)*, 8, 118-127.
5. Tusher, V. G., Tibshirani, R. and Chu, G. (2001) Significance analysis of microarrays applied to the ionizing radiation response. *Proceedings of the National Academy of Sciences of the United States of America*, 98, 5116-5121.
6. Storey, J. D. and Tibshirani, R. (2003) Statistical significance for genomewide studies. *Proceedings of the National Academy of Sciences of the United States of America*, 100, 9440-9445.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11519042B2). An electronic copy of the "Sequence Listing" will also be available from the USPTO upon request and payment of the fee set forth in 37 CFR 1.19(b)(3).

The invention claimed is:

1. A method for detecting at least one RNA transcript, comprising:
    obtaining a biological sample that is collected from a human patient suspected of having lung cancer; and
    detecting, in the biological sample, the presence or absence of at least two RNA transcripts comprising a first RNA transcript expressed by a first nucleic acid sequence having at least 99% identity with SEQ ID NO: 4, and a second RNA transcript expressed by a second nucleic acid sequence having at least 99% identity with SEQ ID NO: 6.

2. The method as claimed in claim 1, wherein the at least two RNA transcripts are mRNA transcripts.

3. The method as claimed in claim 1, wherein the at least two RNA transcripts are detected by hybridization, amplification, or sequencing.

4. The method as claimed in claim 2, wherein the mRNA transcripts are detected by bringing the mRNA transcripts into contact with a probe and/or a primer, and detecting the presence or absence of hybridization to the mRNA transcripts.

5. The method as claimed in claim 2, wherein the mRNA transcripts are detected by detecting the presence or absence of cDNAs obtained from the mRNA transcript transcripts.

6. A method for detecting at least two RNA transcripts, comprising:
    obtaining a biological sample that is collected from a human patient that has been diagnosed with lung cancer; and
    detecting, in the biological sample, the presence or absence of at least two RNA transcripts comprising a first RNA transcript expressed by a first nucleic acid sequence having at least 99% identity with SEQ ID NO:4, and a second RNA transcript expressed by a second nucleic acid sequence having at least 99% identity with SEQ ID NO: 6.

7. The method as claimed in claim 1, further comprising detecting, in the biological sample, the presence or absence of a further RNA transcript expressed by a further nucleic acid sequence having at least 99% identity with SEQ ID NO: 2, 3, 8, 11, 13, 14, 15, 16, 17, 18, 19, 21, 22, 23, 24, 26, 27, 28, 29, 30, 31, 32, 33, 34, 35, 36, 37, 38, 39, 41, 42, 43, 44, 45, 46, 47, 48, 49, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, or 242.

8. The method as claimed in claim 1, further comprising detecting, in the biological sample, the presence or absence of a third RNA transcript expressed by a third nucleic acid sequence having at least 99% identity with SEQ ID NO: 1, 5, 7, or 50.

9. The method as claimed in claim 8, wherein the third nucleic acid sequence has at least 99% identity with SEQ ID NO: 5 or SEQ ID NO: 7.

10. The method according to claim 5, wherein the presence or absence of the cDNAs are detected by bringing the cDNAs into contact with a probe and/or a primer, and detecting the presence or absence of hybridization to the cDNAs.

11. The method as claimed in claim 1, wherein the first nucleic acid sequence is SEQ ID NO: 4, and the second nucleic acid sequence is SEQ ID NO: 6.

12. The method as claimed in claim 11, wherein the at least two RNA transcripts are mRNA transcripts, and
    the mRNA transcripts are detected by detecting the presence or absence of cDNAs obtained from the mRNA transcripts.

13. The method as claimed in claim 11, further comprising determining an expression level of the at least two RNA transcripts in the biological sample.

14. The method as claimed in claim 1, further comprising determining an expression level of the at least two RNA transcripts in the biological sample.

15. A method for detecting at least two RNA transcripts, comprising:
    obtaining a biological sample that is collected from a human patient suspected of having lung cancer; and
    detecting, in the biological sample, the presence or absence of a first RNA transcript expressed by a first nucleic acid sequence having at least 99% identity with SEQ ID NO: 4 by contacting the first RNA transcript or cDNA obtained therefrom with a probe or primers to respectively hybridize to or amplify a region within the first RNA transcript or cDNA obtained therefrom that is defined by a distinct region within the first nucleic acid sequence; and
    detecting, in the biological sample, the presence or absence of a second RNA transcript expressed by a second nucleic acid sequence having at least 99% identity with SEQ ID NO: 6 by contacting the second RNA transcript or cDNA obtained therefrom with a second probe or primers to respectively hybridize to or amplify a region within the second RNA transcript or cDNA obtained therefrom that is defined by a distinct region within the second nucleic acid sequence.

16. The method as claimed in claim 1, wherein no more than 242 specific binding partners are used to detect the at least two RNA transcripts.

* * * * *